United States Patent [19]

Aruga et al.

[11] Patent Number: 5,059,708

[45] Date of Patent: Oct. 22, 1991

[54] PYRENE-RING-CONTAINING OLEFIN COMPOUND, INTERMEDIATE FOR SYNTHESIZING THE OLEFIN COMPOUND AND METHOD OF SYNTHESIZING THE OLEFIN COMOPUND

[75] Inventors: Tamotsu Aruga, Mishima; Masaomi Sasaki, Susono; Tomoyuki Shimada; Hiroshi Adachi, both of Numazu, all of Japan

[73] Assignee: Ricoh Company, Ltd., Tokyo, Japan

[21] Appl. No.: 641,903

[22] Filed: Jan. 16, 1991

[30] Foreign Application Priority Data

| Jan. 19, 1990 | [JP] | Japan | 2-8288 |
| Apr. 9, 1990 | [JP] | Japan | 2-94812 |
| Apr. 27, 1990 | [JP] | Japan | 2-113510 |
| Jul. 31, 1990 | [JP] | Japan | 2-204599 |
| Jul. 31, 1990 | [JP] | Japan | 2-204600 |

[51] Int. Cl.$^5$ .................. C07C 15/38; C07C 15/40; C07F 9/38; C07F 9/40
[52] U.S. Cl. ..................... 558/714; 585/26; 585/500
[58] Field of Search ................. 585/26, 500

[56] References Cited

U.S. PATENT DOCUMENTS

| 4,013,713 | 3/1977 | Weber et al. | 585/26 |
| 4,282,354 | 8/1981 | Van Allan et al. | 585/26 |

OTHER PUBLICATIONS

Akiyama et al.: Bull. Chem. Soc. Japan 44:2231–2236, 1971.

Primary Examiner—Asok Pal
Assistant Examiner—P. Achutamurthy
Attorney, Agent, or Firm—Oblon, Spivak, McClelland, Maier & Neustadt

[57] ABSTRACT

A pyrene-ring-containing olefin compound of formula [I]:

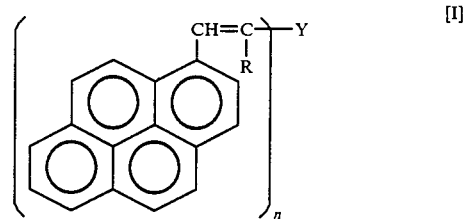

wherein R is a hydrogen atom, an unsubstituted or substituted alkyl group, or an unsubtituted or substituted aryl group; Y is an unsubstituted or substituted aliphatic hydrocarbon group, a cyclic hydrocarbon group, or an aromatic group; and n is an integer of 1 to 3, and when n is 1, Y and R may be bonded to form a ring; an intermediate for producing the above olefin compound, which is a phosphonic acid ester of formula [II]:

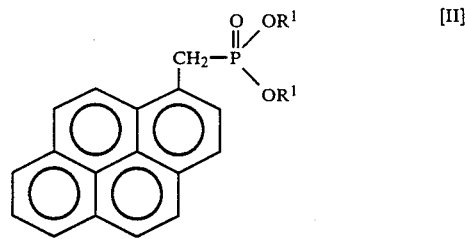

wherein $R^1$ is an alkyl group with 1 to 4 carbon atoms; and a method of producing the above olefin compound are disclosed.

3 Claims, 1 Drawing Sheet

PYRENE-RING-CONTAINING OLEFIN COMPOUND, INTERMEDIATE FOR SYNTHESIZING THE OLEFIN COMPOUND AND METHOD OF SYNTHESIZING THE OLEFIN COMOPUND

BACKGROUND OF THE INVENTION

1. Field of the Invention

The present invention relates to a pyrene-ring-containing olefin compound which is useful as an organic photoconductive material and a material for use in the field of electronics, an intermediate for synthesizing the olefin compound, which is a pyrenyl methyl phosphonic acid ester derivative, and a method of synthesizing the olefin compound.

2. Background of Discussion

Wittig reaction is well known as a conventional method of synthesizing olefin compounds. This reaction provides olefin compounds by the reaction between phosphonium ylide and carbonyl compounds. More specifically, Bull. Chem. Soc. Jpn. 44 2231 (1971) and 45 875 (1972) describe a Wittig reaction utilizing pyrenyl methyl triphenylphosphonium bromide, which provides olefin compounds which are related to the olefin compound according to the present invention. This reaction is excellent in the production of the olefin compounds. However, the olefin compound obtained by this reaction is a mixture of cis- and trans-olefin compounds, so that it has the shortcomings that the reactivity of those olefin compounds with certain ketones is low and that it is difficult to eliminate phosphine oxide produced as a side product in an amount equimolar to that of the olefin compound produced.

SUMMARY OF THE INVENTION

It is therefore a first object of the present invention to provide a novel trans-form pyrene-ring-containing olefin compound which is useful as an organic photoconductive material and a material for use in the field of electronics.

A second object of the present invention is to provide an intermediate for synthesizing the olefin compound, which is a pyrenyl methyl phosphonic acid ester derivative.

A third object of the present invention is to provide a method of selectively synthesizing a trans-form olefin compound, with high purity and high yield under mild conditions, from which a phosphine compound produced as a side product can be easily eliminated.

The first object of the present invention is achieved by a pyrene-ring-containing olefin compound of formula [I]:

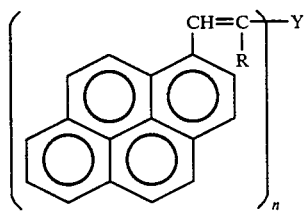

wherein R is a hydrogen atom, an unsubstituted or substituted alkyl group, or an unsubstituted or substituted aryl group: Y is an unsubstituted or substituted aliphatic hydrocarbon group, a cyclic hydrocarbon group, or an aromatic group; and n is an integer of 1 to 3, and when n is 1, Y and R may be bonded to form a ring.

The second object of the present invention is achieved by a phosphonic acid ester of formula [II]:

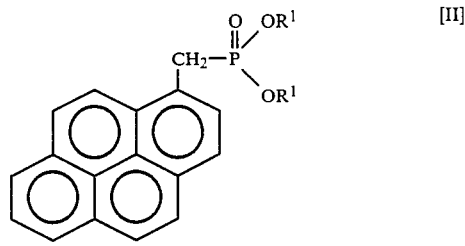

wherein $R^1$ is an alkyl group having 1 to 4 carbon atoms.

The third object of the present invention is achieved by a method of reacting the above phosphonic acid ester of formula [II] with a carbonyl compound of formula [III] in the presence of a basic compound in accordance with the following reaction scheme, which is referred to as Wittig-Horner Reaction:

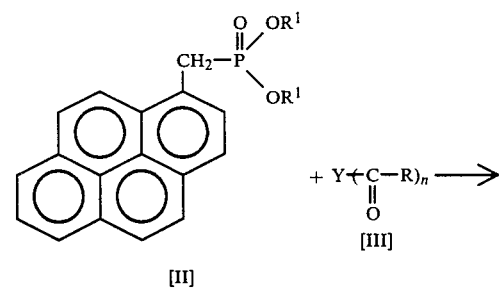

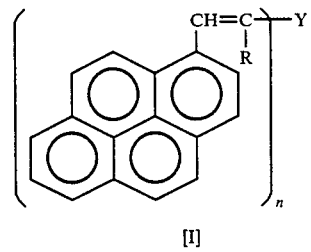

wherein $R^1$ is an alkyl group having 1 to 4 carbon atoms; R is a hydrogen atom, an unsubstituted or substituted alkyl group, or an unsubstituted or substituted aryl group; Y is an unsubstituted or substituted aliphatic hydrocarbon group, a cyclic hydrocarbon group, or an aromatic group; and n is an integer of 1 to 3, and when n is 1, Y and R may be bonded to form a ring.

DETAILED DESCRIPTION OF THE PREFERRED EMBODIMENTS

Figure 1:
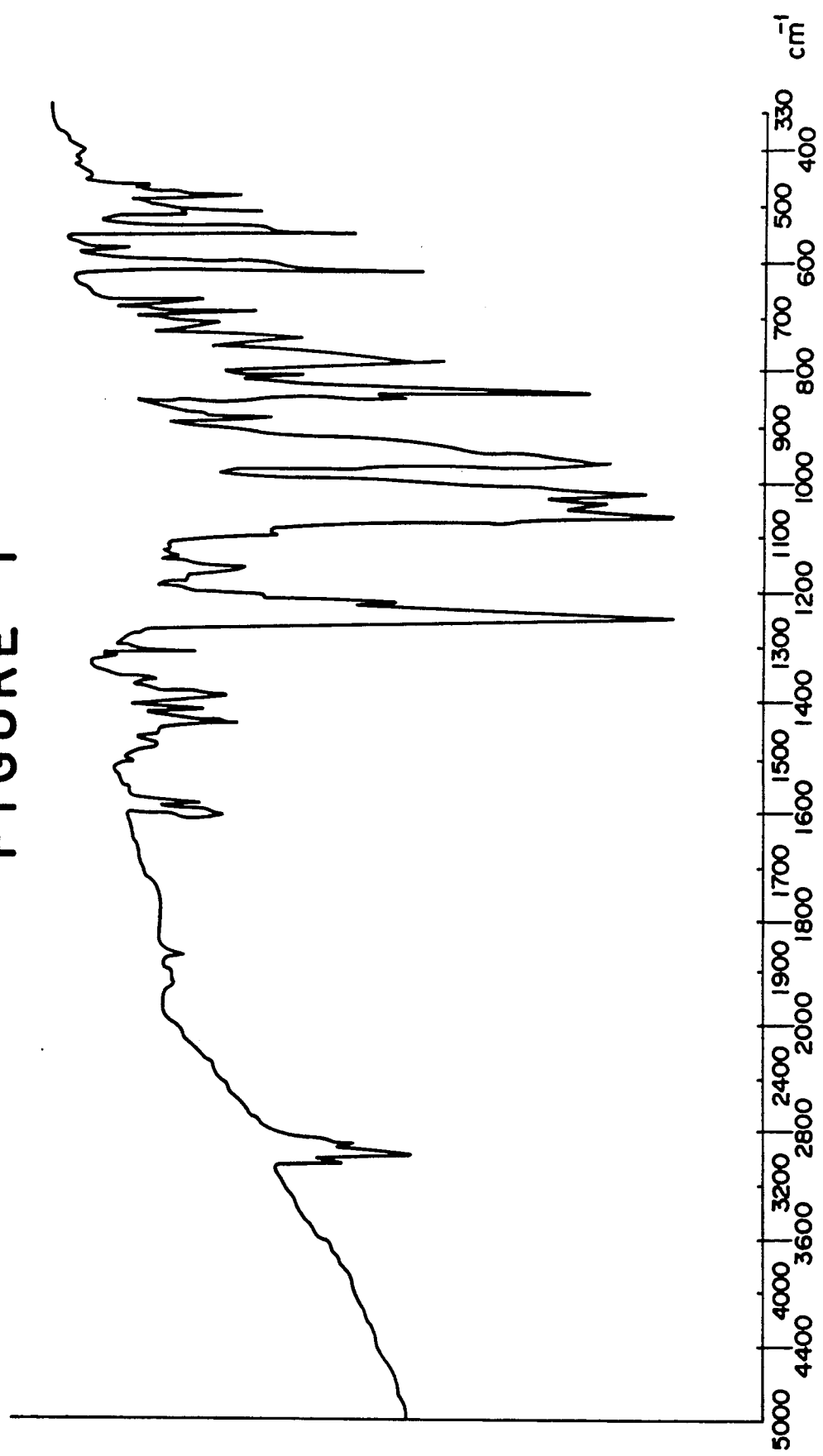
FIG. 1 is an infrared spectrum of diethyl 1-pyrenylmethyl phosphonate prepared in Example 1.

The pyrene-ring-containing olefin compound according to the present invention has formula [I]:

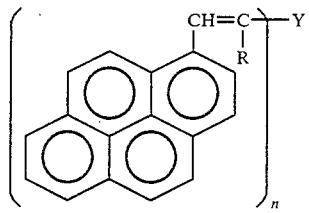

wherein R is a hydrogen atom, an unsubstituted or substituted alkyl group, or an unsubstituted or substituted aryl group; Y is an unsubstituted or substituted aliphatic hydrocarbon group, a cyclic hydrocarbon group, or an aromatic group which may have a substituent; and n is an integer of 1 to 3, and when n is 1, Y and R may be bonded to form a ring.

In the above, the aromatic group represented by Y includes a non-fused carbon cyclic aromatic group such as phenyl group, biphenyl group and terphenyl group; a fused polycyclic hydrocarbon group, and a heterocyclic aromatic group. It is preferable that in the fused polycyclic hydrocarbon group, the number of carbon atoms by which the ring is formed be 18 or less. Specific examples of the fused polycyclic hydrocarbon group include pentalenyl group, indenyl group, naphthyl group, azulenyl group, heptalenyl group, biphenyl group, as-indacenyl group, fluorenyl group, fluorenyl group, s-indacenyl group, acenaphthylenyl group, pleiadenyl group, acenaphthenyl group, phenalenyl group, phenanthrenyl group, anthracenyl group, acephenanthrenyl group, aceanthrylenyl group, triphenylenyl group, pyrenyl group, chrysenyl group, and naphthacenyl group.

Examples of the heterocyclic aromatic group include thienyl group, furyl group, 2-pyridyl group, 4-pyridyl group, 3-indolyl group, 2-thinolynyl group, 3,4-benzpyranyl group, acridinyl group, thiazolyl group, benzthiazolonyl group, 9-methylcarbazolyl group, 9-propylcarbazolyl group, 9-phenylcarbazolyl group, 9-tolylcarbazolyl group.

The above aromatic groups may have a substituent. Examples of the substituent include as follows:

(1) a halogen atom, cyano group, and nitro group; and (2) alkyl group, preferably alkyl group having 1 to 12 carbon atoms, more preferably alkyl group having 1 to 8 carbon atoms, and most preferably alkyl group having 1 to 4 carbon atoms. These alkyl group may further include a fluorine atom, hydroxyl group, cyano group, alkoxyl group having 1 to 4 carbon atoms, phenyl group, or phenyl group which is substituted with a halogen atom, alkyl group having 1 to 4 carbon atoms, or alkoxyl group having 1 to 4 carbon atoms. Specific examples of the alkyl group include methyl group, ethyl group, n-propyl group, i-propyl group, t-butyl group, s-butyl group, n-butyl group, i-butyl group, trifluoromethyl group, 2-hydroxyethyl group, 2-cyanoethyl group, 2-ethoxyethyl group, 2-methoxyethyl group, benzyl group, 4-chlorobenzyl group, 4-methylbenzyl group, 4-methoxybenzyl group and 4-phenylbenzyl group.

(3) alkoxyl group (—$OR^1$), in which $R^1$ is the same alkyl group as that defined in (2) above. Specific examples of the alkoxyl group include methoxy group, ethoxy group, n-propoxy group, i-propoxy group, t-butoxy group, n-butoxy group, s-butoxy group, i-butoxy group, 2-hydroxyethoxy group, 2-cyanoethoxy group, benzyloxy group, 4-methylbenzyloxy group, and trifluoromethoxy group.

(4) aryloxy group. Specific examples of the aryloxy group include phenyl group and naphthyl group. The aryloxy group may have a substituent such as an alkoxy group having 1 to 4 carbon atoms, an alkyl group having 1 to 4 carbon atoms, or a halogen. Specific examples of these aryloxy group include phenoxy group, 1-naphthyloxy group, 2-naphthyloxy group, 4-methylphenoxy group, 4-methoxyphenoxy group, 4-chlorophenoxy group, and 6-methyl-2-naphthyloxy group.

(5) alkylmercapto group (—$SR^1$), in which $R^1$ is the same alkyl group as that defined in (2) above. Specific examples of the alkylmercapto group include methylthio group, ethylthio group, phenylthio group, and p-methylphenylthio group.

wherein $R^2$ and $R^3$ each represent hydrogen, the alkyl group defined in (2), or an aryl group. Specific examples of the aryl group include phenyl group and biphenyl group, and naphthyl group. These aryl group may have a substituent such as alkoxyl group having 1 to 4 carbon atoms, alkyl group having 1 to 4 carbon atoms, or a halogen. $R^2$ and $R^3$ may be bonded to each other or to the carbon atoms in the aryl group to form a ring. Specific examples of the above group include amino group, diethylamino group, diethylamino group, N-methyl-N-phenylamino group, N,N-diphenylamino group, N,N-di(p-tolyl)amino group, dibenzylamino group, piperidino group, morpholino group, and juloridyl group.

(7) alkylenedioxy or alkylenedithio group such as methylene dioxy group or methylene dithio group.

The intermediate for synthesizing the pyrene-ring-containing olefin compound of formula [I] is a phosphonic acid ester of formula [II]:

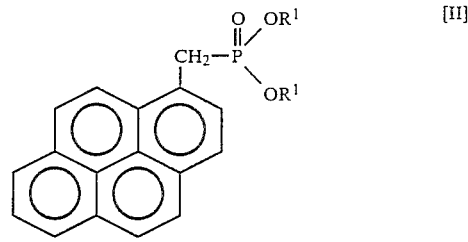

wherein $R^1$ is an alkyl group having 1 to 4 carbon atoms.

Specific examples of the above alkyl group are methyl group, ethyl group, propyl group, isopropyl group, n-butyl group, iso-butyl group, sec-butyl group, and tert-butyl group.

The phosphonic acid ester of formula [II] can be prepared in accordance with the following reaction scheme:

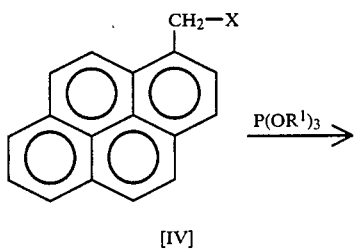

[IV]

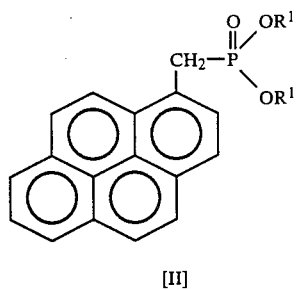

[II]

wherein R¹ is the same as that defined in formula [II].

In the above reaction, a halomethyl compound of formula [IV], which is a starting material for synthesizing the phosphonic acid ester of formula [II], can be prepared by a conventional method. Further, in this reaction, the reaction between the halomethyl compound of formula [IV] and the trialkyl phosphite of P(OR¹)₃ is carried out without solvent, generally at 80° C. to 160° C., preferably at 100° C. to 140° C., with the molar ratio of the trialkyl phosphite to the halomethyl compound [IV] generally being 1 to 100:1, preferably 2 to 4:1.

The pyrene-ring-containing olefin compound of formula [I] can be synthesized by allowing the above phosphonic acid ester of formula [II] with a carbonyl compound of formula [III] in the presence of a basic compound in accordance with the following reaction scheme, which is referred to as Wittig-Horner Reaction:

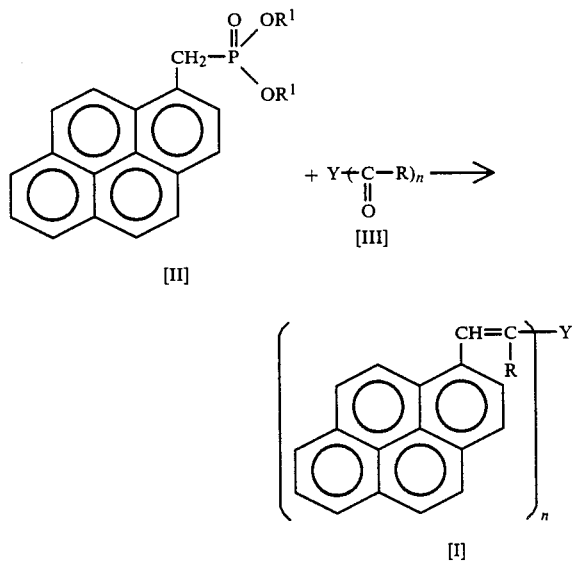

In the above formulas, R, R¹ and Y are the same as those defined previously.

In the above reaction, since the phosphonic acid ester of formula [II] has strong neucleophilic properties, it can react with varieties of aldehyde and ketones under mild conditions to produce the olefin compounds of the formula [I] selectively in a trans form with high purity and high yield. Furthermore, a phosphine compound produced as a side product in the above reaction is water-soluble, so that the elimination of the side product is easy.

As the basic compound for use in the above reaction, alkoxides of an alkali metal such as lithium and sodium, alkyl alkali metals, and alkali metal hydrides can be employed. As the solvent for use in the above reaction, polar solvents such as N,N-dimethylformamide and dimethylsulfoxide, and non-polar solvents such as ethanol, benzene, and tetrahydrofuran can be employed.

When preparing the olefin compound of formula [I] in practice, the phosphonic acid ester of formula [II] and the carbonyl compound of formula [III] are dissolved in any of the above solvents. To this mixture, any of the above basic compounds is gradually added with stirring. The reaction easily proceeds at room temperature.

Examples of the carbonyl compound of formula [III],

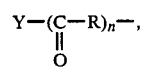

in which Y is an aliphatic hydrocarbon, include saturated aldehydes such as acetaldehyde, propionaldehyde, butanal, 2-methylpropanal, pentanal, hexanal, heptanal, octanal, nonanal, and decanal; unsaturated aldehydes such as acrylaldehyde, crotonaldehyde, methacrylaldehyde, 2-methyl-2-butynal propynal, and 2-butynal; and unsaturated ketones such as ethylidene acetone. These compounds may have the same substituents as set forth in the case of the aromatic groups represented by Y in formula [I]. Examples of such compounds are phenyl acetaldehyde and cinnamaldehyde.

Examples of the carbonyl compound of formula [III], in which Y is an aliphatic hydrocarbon, include cyclohexane carbaldehyde, safranal, α-ionone, cyclohexanone, 2-cyclo-hexene-1-one.

The alkyl group represented by R in formula [III] is the same as defined in formula [I].

Examples of the aryl group represented by R in formula [III] are phenyl group, biphenyl group and naphthyl group.

Representative examples of the carbonyl compound of formula [III] when n is 2 are phthalaldehyde, isophthalaldehyde, terephthalaldehyde, naphthalenedicarbaldehyde, 2,4-hexadiene-1,6-dial.

Representative examples of the carbonyl compound of formula [III] when n is 3 are 1,3,5-triacetylbenzene and 4,4′,4″-triacetyltriphenylamine.

The features of the present invention will become apparent in the course of the following description of exemplary embodiments, which are given for illustration of the invention and are not intended to be limiting thereof.

EXAMPLE 1

[Preparation of Diethyl 1-pyrenylmethyl phosphonate]

120 g (0.48 moles) of 1-chloromethylypyrene was dissolved in 500 ml of triethyl phosphite. This reaction mixture was then heated with stirring at 125° C. to 140° C. for 5 hours. In the course of this reaction, ethylene chloride generated was removed from the reaction mixture. The reaction mixture was then cooled. 370 ml of n-hexane was then added to the reaction mixture, so that crystals were caused to separate out. The crystalline product was separated from the reaction mixture by filtration, washed with 300 ml of n-hexane two times, and dried with application of heat under reduced pressure, whereby 151.4 g (89.7%) of a crude product of diethyl 1-pyrenylmethyl phosphonate was obtained. The thus obtained crude product of diethyl 1-pyrenylmethyl phosphonate was recrystallized from a mixed solvent of n-hexane and ethyl acetate, whereby pure diethyl 1-pyrenyl phosphonate was obtained in the form of white needles with a melting point of 115.0° C. to 116.0° C.

The results of elemental analysis of the diethyl 1-pyrenyl phosphonate were as follows:

|  | Found | Calculated |
|---|---|---|
| % C | 71.66 | 71.58 |
| % H | 5.95 | 6.01 |

The infrared- spectrum thereof, which is shown in FIG. 1, was measured by use of a KBr tablet. The characteristic absorptions were found at 1245 cm$^{-1}$ ($\nu_{p=o}$), 1150 cm$^{-1}$ ($\nu_{c\text{-}o\text{-}(p)}$), and 1025 cm$^{-1}$ ($\nu_{p\text{-}o\text{-}(c)}$).

EXAMPLE 2

[Preparation of Olefin Compound No. 1, 1-(4-chlorostyryl)pyrene]

2.47 g (7 mmol) of diethyl 1-pyrenylmethylphosphonate and 0.99 g (7 mmol) of 4-chlorobenzaldehyde were dissolved with stirring in 25 ml of N,N-dimethylformamide. To this reaction mixture, 1.62 g (7×1.2 mmol) of sodium methylate (28 wt. % methanol solution of sodium methylate) was gradually added in such a manner that the temperature of the reaction mixture did not exceed 30° C.). The reaction mixture was then stirred at room temperature for 1 hour, neutralized with acetic acid, and diluted with about 300 ml of water. Crystals separated out. The crystals were separated by filtration, washed with water, dried and then purified by column chromatography two times. In the first time, the purification was carried out on a column of silica gel, using a mixed solvent of toluene/n-hexane (1/1) as the developing solvent, and in the second time, the purification was carried out on a column of silica gel, using a mixed solvent of toluene/n-hexane (½) as the developing solvent, whereby yellow 1-(4-chlorostyryl)pyrene was obtained with a yield of 2.21 g (93.5%).

The thus obtained 1-(4-chlorostyryl)pyrene was recrystallized from a mixed solvent of toluene and n-hexane, so that pyrene-ring containing olefin compound No. 1 according to the present invention, 1-(4-chlorostyryl)pyrene with a melting point of 157.5° C. to 158.5° C., was obtained in the form of yellow cotton-thread-like needles.

The results of elemental analysis of the 1-(4-chlorostyryl)pyrene were as follows:

|  | Found | Calculated |
|---|---|---|
| % C | 85.25 | 85.06 |
| % H | 4.17 | 4.46 |

The infrared spectrum thereof was measured by use of a KBr tablet. A characteristic absorption was at 965 cm$^{-1}$ ($\delta_{CH,\ trans\text{-}olefin}$).

EXAMPLES 3 to 10

Pyrene-ring-containing olefin compounds No. 2 to No. 9 according to the present invention, which are given in TABLE 1, were prepared in the same manner as in Example 2 by allowing diethyl 1-pyrenylmethylphosphonate to react with the aldehyde compounds given in TABLE 1.

TABLE 1

| Example | Aldehyde employed | Olefin Compound | m.p. (°C.) |
|---|---|---|---|
| 3 | OHC—⌬—N(Et)₂ | No. 2 | 149.5~150.3 |
| 4 | OHC—⌬—N(—⌬—CH₃)₂ | No. 3 | 228.8~300.5 |
| 5 | OHC-indole-Et | No. 4 | 202.0~203.0 |

TABLE 1-continued

| Example | Aldehyde employed | Olefin Compound | m.p. (°C.) |
|---------|-------------------|-----------------|------------|
| 6 | | No. 5 | 186.0~187.0 |
| 7 | | No. 6 | >280 |
| 8 | | No. 7 | >280 |
| 9 | | No. 8 | 198~200 |
| 10 | | No. 9 | 148~149.0 |

APPLICATION EXAMPLE 7.5 parts by weight of a bisazo pigment with the following formula, serving as a charge generating layer, and 500 parts by weight of a polyester resin tetrahydrofuran solution containing a polyester resin (Trademark "Vylon 200" made by Toyobo Company, Ltd.) in an amount of 0.5 wt. %, were mixed and ground in a ball mill:

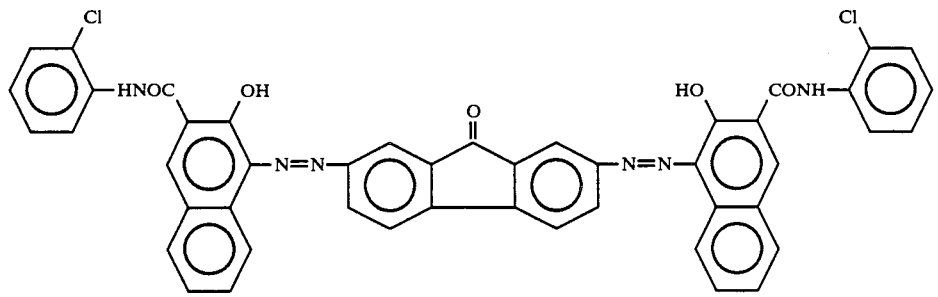

This dispersion was coated on an aluminum-deposited polyester film by a doctor blade and was then dried at room temperature, so that a charge generation layer with a thickness of about 1 μm was formed on the aluminum-deposited polyester film.

Furthermore, one part by weight of a polycarbonate resin (Trademark "Panlite K-1300" made by Teijin Limited), and 8 parts by weight of tetrahydrofuran were mixed to prepare a resin dispersion. In this dispersion, one part by weight of pyrene-ring-containing olefin compound No. 5, prepared in Example 6, serving as a charge transporting material, was dispersed. This dispersion was coated on the above prepared charge generation layer by a doctor blade and was then dried at 80° C. for 2 minutes, and then at 120° C. for 5 minutes, so that a charge transport layer with a thickness of about 20 μm was formed on the charge generation layer. Thus a layered type electrophotographic photoconductor was prepared.

The thus prepared electrophotographic photoconductor was charged negatively in the dark under application of −6 kV of corona charge for 20 seconds and was then allowed to stand in the dark for 20 seconds without applying any charge thereto, and the surface potential Vo (Volt) of the photoconductor was measured by a Paper Analyzer (Trademark "Model SP428" made by Kawaguchi Works Co., Ltd.). The photoconductor was then illuminated by a tungsten lamp in such a manner that the illuminance on the illuminated surface of the photoconductor was 4.5 lux, so that the exposure $E_{\frac{1}{2}}$ (lux.sec) required to reduce the initial surface potential Vo(Volt) to $\frac{1}{2}$ the initial surface potential Vo(Volt) was also measured. The result was that Vo was −1121 Volts, and $E_{\frac{1}{2}}$ was 0.89 lux.sec.

The above electrophotographic photoconductor was negatively charged by a commercially available copying machine and a latent electrostatic image was formed on the photoconductor and was developed to a visible toner image by a positively charged dry type toner. The thus developed toner image was transferred electrostatically to a high quality transfer sheet and was fixed thereto. As a result, a clear toner image was formed on the transfer sheet. In the case where a wet type developer was used instead of the dry type toner, a clear image was also obtained.

What is claimed is:

1. A pyrene-ring-containing olefin compound of formula [I]:

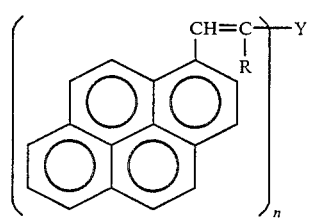

wherein R is a hydrogen atom, an unsubstituted or substituted alkyl group, or an unsubstituted or substituted aryl group; Y is an unsubstituted or substituted aliphatic hydrocarbon group, a cyclic hydrocarbon group, or an aromatic group; and n is an integer of 1 to 3, and when n is 1, Y and R may be bonded to form a ring.

2. A phosphonic acid ester of formula [II]:

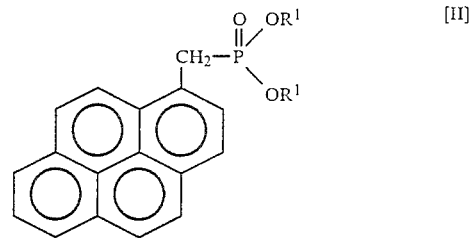

wherein $R^1$ is an alkyl group having 1 to 4 carbon atoms.

3. A method of producing a pyrene-ring-containing olefin compound of formula [I]:

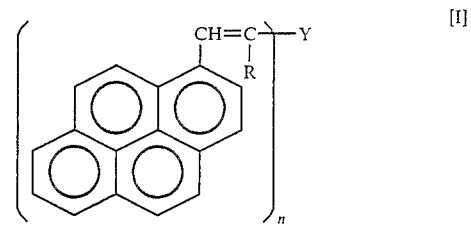

wherein R is a hydrogen atom, an unsubstituted or substituted alkyl group, or an unsubstituted or substituted aryl group; Y is an unsubstituted or substituted aliphatic hydrocarbon group, a cyclic hydrocarbon group, or an aromatic group; and n is an integer of 1 to 3, and when n is 1, Y and R may be bonded to form a ring, by reacting a phosphonic acid ester of formula [II] with a carbonyl compound of formula [III] in the presence of a basic compound in accordance with the following reaction scheme:

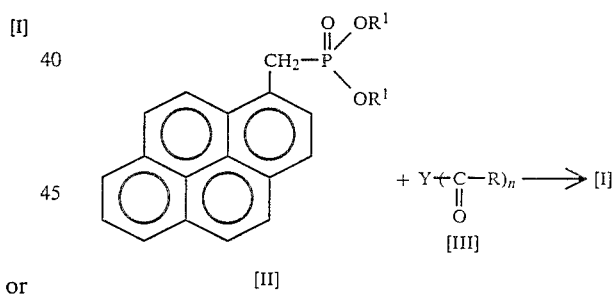

wherein $R^1$ is an alkyl group having 1 to 4 carbon atoms; R is a hydrogen atom, an unsubstituted or substituted alkyl group, or an unsubstituted or substituted aryl group; Y is an unsubstituted or substituted aliphatic hydrocarbon group, a cyclic hydrocarbon group, or an aromatic group; and n is an integer of 1 to 3, and when n is 1, Y and R may be bonded to form a ring.

* * * * *

UNITED STATES PATENT AND TRADEMARK OFFICE
CERTIFICATE OF CORRECTION

PATENT NO. : 5,059,708
DATED : October 22, 1991
INVENTOR(S) : Tamotsu ARUGA ET AL.

It is certified that error appears in the above-identified patent and that said Letters Patent is hereby corrected as shown below:

Column 3, line 29, "fluorenyl group" delete duplicate --fluorenyl group--

Column 4, line 36, "diethylamino group" delete duplicate --diethylamino group--

Column 6, line 36, "2-methyl-2-butynal propynal," should read --2-methyl-2-butynal, propynal,--

Column 8, line 11, "toluene/n-hexane (½)as the" should read --toluene/n-hexane (1/2) as the--

Column 8, line 16, "pyrene-ring containing olefin" should read --pyrene-ring-containing olefin--

Signed and Sealed this

Ninth Day of November, 1993

Attest:

BRUCE LEHMAN

Attesting Officer

Commissioner of Patents and Trademarks